(12) United States Patent
Wako et al.

(10) Patent No.: US 7,801,186 B2
(45) Date of Patent: Sep. 21, 2010

(54) LIGHT SOURCE

(75) Inventors: Sugio Wako, Ueda (JP); Atsushi Koyama, Ueda (JP); Xiongfei Zhang, Ueda (JP); Hiroshi Matsuura, Chiyoda-ku (JP); Satoru Abe, Chiyoda-ku (JP); Takeshi Takagi, Chiyoda-ku (JP)

(73) Assignees: The Furukawa Electric Co., Ltd., Tokyo (JP); Totoku Electric Co., Ltd., Tokyo (JP)

( * ) Notice: Subject to any disclaimer, the term of this patent is extended or adjusted under 35 U.S.C. 154(b) by 0 days.

(21) Appl. No.: 11/952,647

(22) Filed: Dec. 7, 2007

(65) Prior Publication Data

US 2008/0123695 A1  May 29, 2008

Related U.S. Application Data

(63) Continuation of application No. PCT/JP2006/311448, filed on Jun. 7, 2006.

(30) Foreign Application Priority Data

Jun. 7, 2005 (JP) ............................. 2005-166364
Oct. 3, 2005 (JP) ............................. 2005-289551

(51) Int. Cl.
*H01S 3/30* (2006.01)
(52) U.S. Cl. .......................... 372/6; 372/50.11; 372/69; 372/71; 372/102
(58) Field of Classification Search ...................... 372/6, 372/50.11, 69, 71, 102
See application file for complete search history.

(56) References Cited

U.S. PATENT DOCUMENTS

| | | | |
|---|---|---|---|
| 5,659,644 A * | 8/1997 | DiGiovanni et al. | 385/31 |
| 5,809,048 A | 9/1998 | Shichijyo et al. | |
| 6,052,392 A | 4/2000 | Ueda et al. | |
| 6,268,954 B1 * | 7/2001 | Cheng | 359/337 |
| 6,751,241 B2 * | 6/2004 | Davis et al. | 372/6 |
| 7,106,762 B1 * | 9/2006 | Jiang et al. | 372/6 |
| 2002/0093998 A1 | 7/2002 | Kimura et al. | |
| 2002/0118715 A1 | 8/2002 | Kimura et al. | |
| 2003/0128728 A1 | 7/2003 | Shimizu et al. | |
| 2004/0028091 A1 * | 2/2004 | Baev et al. | 372/6 |
| 2004/0196874 A1 * | 10/2004 | Spiegelberg et al. | 372/6 |
| 2005/0243409 A1 * | 11/2005 | Harter et al. | 359/341.1 |

FOREIGN PATENT DOCUMENTS

| | | |
|---|---|---|
| JP | 2-87587 | 3/1990 |
| JP | 4-359485 | 12/1992 |

(Continued)

*Primary Examiner*—Minsun Harvey
*Assistant Examiner*—Yuanda Zhang
(74) *Attorney, Agent, or Firm*—Oblon, Spivak, McClelland, Maier & Neustadt, L.L.P.

(57) ABSTRACT

A spatial coupling provided between an amplified-light waveguide and an output-light waveguide includes a wavelength selecting element that selectively transmits a light having a desired wavelength band out of a spontaneous emission light generated in the amplified-light waveguide and a lens unit that couples the spontaneous emission light to the wavelength selecting unit. An input-side light reflecting unit provided between a semiconductor pumping laser and the amplified-light waveguide and an output-side light reflecting unit formed on an output side of the spatial coupling unit form a laser resonator.

6 Claims, 6 Drawing Sheets

FOREIGN PATENT DOCUMENTS

| | | |
|---|---|---|
| JP | 7-311319 | 11/1995 |
| JP | 8-213686 | 8/1996 |
| JP | 10-190097 | 7/1998 |
| JP | 2000-353838 | 12/2000 |
| JP | 2001-230476 | 8/2001 |
| JP | 2001-326404 | 11/2001 |
| JP | 2002-141607 | 5/2002 |
| JP | 2002-141608 | 5/2002 |
| JP | 2002-270928 | 9/2002 |
| JP | 2003-258732 | 9/2003 |
| JP | 2003-283036 | 10/2003 |
| JP | 2003-309309 | 10/2003 |
| JP | 2005-12008 | 1/2005 |
| JP | 2005-79197 | 3/2005 |

\* cited by examiner

US 7,801,186 B2

LIGHT SOURCE

CROSS-REFERENCE TO RELATED APPLICATIONS

This application is a continuation of PCT/JP2006/311448 filed on Jun. 7, 2006, the entire content of which are incorporated herein by reference.

BACKGROUND OF THE INVENTION

1. Field of the Invention

The present invention relates to a light source for a laser microscope, a biomedical analyzer, a precision measurement device, and the like.

2. Description of the Related Art

Conventionally, a light source used for, for example, a laser microscope, a fluorescence analyzer for biomedicine, a biological analyzer for biomedicine, and a precision measurement device, includes a semiconductor laser or a light source that generates a harmonic light by pumping an SHG (second harmonic generation) element or a THG (third harmonic generation) element that serves as a harmonic generating element such as a nonlinear optical crystal with a semiconductor laser. A light generated by the semiconductor laser has a specific wavelength, and a harmonic light generated by the SHG element or the THG element has a wavelength of a half or a third of a wavelength of a semiconductor laser used for pumping.

An optical fiber laser employing an optical fiber is disclosed as a light source that generates a light having a desired wavelength (see, for example, Patent Document 1:Japanese Patent Application Laid-open No. 2005-12008).

In an apparatus such as a laser microscope, for example, a light having a wavelength between 530 nanometers and 600 nanometers is necessary to perform fluorescence analysis of protein. To generate a light having a wavelength within such a wavelength band with the SHG element, a light source that generates a light having a wavelength between 1060 nanometers and 1200 nanometers is necessary.

However, a conventional light source has a problem that a light output is not stable enough. Particularly, a light source used in combination with a harmonic generating element results in a problem that an output of a harmonic light generated by the harmonic generating element is unstable.

SUMMARY OF THE INVENTION

It is an object of the present invention to at least partially solve the problems in the conventional technology.

A light source according to one aspect of the present invention includes a semiconductor pumping laser that outputs a pumping laser light; a pumping-light waveguide that guides the pumping laser light output from the semiconductor pumping laser; an amplified-light waveguide that is connected to the pumping-light waveguide, and that is doped with an amplification medium that is pumped by the pumping laser light so that a spontaneous emission light in a desired wavelength band is generated; an output-light waveguide that guides the spontaneous emission light output from the amplified-light waveguide; a spatial coupling unit provided between the amplified-light waveguide and the output-light waveguide, which includes a wavelength selecting element that selectively transmits a light having a desired wavelength band out of the spontaneous emission light and a lens unit that couples the spontaneous emission light to the wavelength selecting unit; an input-side light reflecting unit that is provided between the semiconductor pumping laser and the amplified-light waveguide; and an output-side light reflecting unit that is formed on an output side of the spatial coupling unit. The input-side light reflecting unit and the output-side light reflecting unit form a laser resonator that includes the amplified-light waveguide and the spatial coupling unit.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Exemplary embodiments of a light source according to the present invention are explained in detail below with reference to the accompanying drawings. Note that the present invention is not limited to the embodiments.

Figure 1:
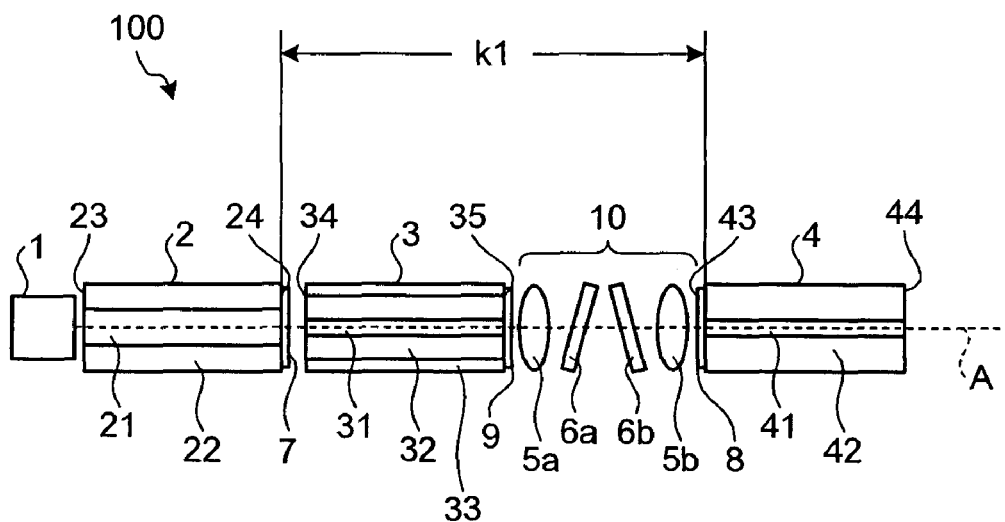
FIG. 1 is a schematic diagram of a light source according to a first embodiment of the present invention.

FIG. 1 is a schematic diagram of a light source 100 according to a first embodiment of the present invention. The light source 100 includes a semiconductor pumping laser 1, a multimode optical fiber 2, a double-clad optical fiber 3, a single-mode optical fiber 4, a spatial coupling unit 10, a dielectric multilayer filter 7, and a dielectric multilayer filter 8. The multimode optical fiber 2 serving as a pumping-light waveguide guides a pumping laser light having a wavelength of 915 nanometers output from the semiconductor pumping laser 1. The double-clad optical fiber 3 serving as an amplified-light waveguide is connected to the multimode optical fiber 2 doped with Ytterbium (Yb) ions serving as an amplification medium that is pumped by the pumping laser light output from the multimode optical fiber 2 to generate a spontaneous emission light having a wavelength band between 1060 nanometers to 1200 nanometers. The single-mode optical fiber 4 serving as an output-light waveguide guides the spontaneous emission light output from the double-clad optical fiber 3. The spatial coupling unit 10 is provided between the double-clad optical fiber 3 and the single-mode optical fiber 4. The spatial coupling unit 10 includes etalon filters 6a and 6b serving as a wavelength selecting element that selectively transmits a light of a desired wavelength from the spontaneous emission light, a light having a center wavelength of 1100 nanometers and a full width half maximum equal to or narrower than 10 nanometers in the present embodiment, and spherical lenses 5a and 5b serving as a lens unit for coupling the spontaneous emission light to the etalon filters 6a and 6b. The dielectric multilayer filter 7 serving as an input-side light reflecting unit is formed on an output facet 24 of the multimode optical fiber 2. The dielectric multilayer filter 8 serving as an output-side light reflecting unit is formed on an input facet 43 of the single-mode optical fiber 4. The dielectric multilayer filters 7 and 8 form a laser resonator k1 including the double-clad optical fiber 3 and the spatial coupling unit 10.

The semiconductor pumping laser 1 outputs a pumping laser light having a wavelength of 915 nanometers with an intensity approximately between a several hundred of milliwatts and 5 watts. For pumping the Ytterbium ions, the pumping laser beam should preferably have a wavelength between 900 nanometers to 1000 nanometers. The multimode optical fiber 2 includes a core region 21 having a core diameter of 50 micrometers and a cladding region 22 formed on an outer circumference of the core region 21 and having an outer diameter of 125 micrometers. The pumping laser light input to the input facet 23 propagates through the core region 21 and output from the output facet 24 on which the dielectric multilayer filter 7 is formed. If the core region 21 has a core diameter equal to or larger than 50 micrometers, a pumping laser light having an intensity of several hundred of milliwatts can be efficiently coupled and propagate.

The double-clad optical fiber 3 includes a core region 31 with a core diameter of 6 micrometers doped with Yb ions, an inner cladding layer 32 formed on the outer circumference of the core region 31 and having a refractive index smaller than that of the core region 31 with an outer diameter of 130 micrometers, and an outer cladding layer 33 formed on an outer circumference of the inner cladding layer 32 and having a refractive index smaller than that of the inner cladding layer 32 with an outer diameter of 250 micrometers. The Yb ions injected into the core region 31 of the double-clad optical fiber 3 are pumped by the pumping laser light that is input to an input facet 34 and propagates through the core region 31 and the inner cladding layer 32. As a result, a spontaneous emission light having a wavelength band between 1060 nanometers to 1200 nanometers is generated. The spontaneous emission light propagates through the core region 31, and is output from an output facet 35. As the double-clad optical fiber 3, an optical fiber can be used, which includes a core region with a core diameter equal to or larger than 5 micrometers and equal to or smaller than 100 micrometers made of a silica doped with a rare-earth element, an inner cladding layer with a diameter larger than the core diameter and equal to or smaller than 1000 micrometers made of a silica, and an outer cladding layer with an outer diameter larger than the diameter of the inner cladding layer and equal to or smaller than 2000 micrometers made of a resin or a silica.

In the spatial coupling unit 10, the spherical lens 5a couples the spontaneous emission light output from the output facet 35 of the double-clad optical fiber 3 to the etalon filters 6a and 6b. The light having a center wavelength of 1100 nanometers and a full width half maximum of equal to or narrower than 10 nanometers is selectively transmitted through the etalon filters 6a and 6b with a transmissivity equal to or more than 70% at the center wavelength, and is coupled to the single-mode optical fiber 4 with the spherical lens 5a. The single-mode optical fiber 4 includes a core region 41 having a core diameter of 10 micrometers and a cladding region 42 formed on an outer circumference of the core region 41 and having a refractive index smaller than that of the core region 41 with an outer diameter of 125 micrometers. In the light source according to the first embodiment, the double clad optical fiber 3 and the single-mode optical fiber 4 with different diameters are optically coupled by the spherical lenses 5a and 5b with a high efficiency. The material of the spherical lenses 5a and 5b is a silica or a glass such as BK7 and borosilicate glass.

The etalon filter 6a is a narrow-band filter that employs multiple optical interferences, and that has high transmissivity. The etalon filter 6a is arranged in a way that the angle of the etalon filter 6a with respect to the optical axis A of the spatial coupling unit 10 is adjusted, so that the center wavelength of a transmission band is kept 1100 nanometers. The etalon filter 6b is arranged such that the etalon filter 6b is symmetrical to the etalon filter 6a with respect to an inclination angle to a plane perpendicular to the optical axis A. Therefore, the optical axis of a light transmitted through the etalon filters 6a and 6b is kept on the optical axis A before and after a transmission. If the etalon filters are thin, the optical axis can be kept only with the etalon filter 6a. The light source 100 can include an inclination angle adjusting mechanism for adjusting the inclination angles of the etalon filters 6a and 6b to desired values.

In the light source 100 according to the first embodiment, the dielectric multilayer filter 8 is formed on the input facet 43 of the single mode optical fiber 4, and the dielectric multilayer filters 7 and 8 form the laser resonator k1 that includes the double-clad optical fiber 3 and the spatial coupling unit 10. The dielectric multilayer filter 7 has a reflectivity of 95% at a wavelength of 1100 nanometers, and has a reflectivity of 5% at a wavelength of 915 nanometers that is the wavelength of the pumping laser light. The dielectric multilayer filter 8 has a reflectivity equal to or more than 4% and equal to or less than 70% at the wavelength of 1100 nanometers. If the wavelength of the etalon filter is equal to or longer than 1075 nanometers as in the case of the first embodiment, the reflectivity should preferably be equal to or more than 40% and equal to or less than 70%. The dielectric multilayer filter 8 has a reflectivity of 5% and a transmissivity of 95% or more at the wavelength of 915 nanometers of the pumping laser light, as in the case of the dielectric multilayer filter 7. Each of the dielectric multilayer filters 7 and 8 is formed by alternately depositing a high-refractive dielectric film of, for example, $Ta_2O_5$ and a low-refractive dielectric film of, for example, $SiO_2$. The above desired characteristics can be realized by appropriately designing the films in consideration of a thickness of each layer and the number of layers to be deposited.

The dielectric multilayer filters 7 and 8 having the above reflectivities causes the laser resonator k1 to oscillate the spontaneous emission light of the wavelength of 1100 nanometers transmitted through the etalon filters 6a and 6b, the single-mode optical fiber 4 guides the laser light having the wavelength of 1100 nanometers, and the laser light is output from the output facet 44. A typical etalon filter has a plurality of transmission bands at an optical frequency interval that is determined by a thickness of the etalon filter. When each of the thicknesses of the etalon filters 6a and 6b is between 20 micrometers and 30 micrometers, the optical frequency interval becomes wider so that a single transmission band for a main laser oscillation peak in a frequency band of the spontaneous transmission light generated by the YB ions can be realized. Accordingly, a laser light having a substantially single wavelength can be generated by oscillation.

The light source 100 includes the double-clad optical fiber 3 and the spatial coupling unit 10 that includes the etalon filters 6a and 6b. This suppresses, for example, an unstable laser oscillation resulting from a mode hopping caused between longitudinal modes due to an oscillation of an unnecessary longitudinal mode, which leads to a stable laser oscillation of a stable longitudinal mode at a wavelength of 1100 nanometers. Accordingly, a stable output of a laser light can be obtained. The full width half maximum of the transmission band of the etalon filters 6a and 6b is equal to or shorter than 10 nanometers. If the full width half maximum is equal to or narrower than 3 nanometers, the transmission band is limited, so that the output can be more stable. Furthermore, a dielectric multilayer AR (antireflection) coating 9 for preventing a reflection is formed on the output facet 35 of the double-clad optical fiber 3 of the light source 100. This prevents formation of an unnecessary resonator other than the laser resonator k1 due to a reflection at the facets in the laser resonator k1. Accordingly, an unstable laser oscillation can be prevented that would be otherwise caused because of the unnecessary resonator, and that has a longitudinal mode interval, for example, equal to or more than 0.1 nanometer, which is larger than a longitudinal mode interval of the laser resonator k1. Accordingly, generation of optical intensity noise can be prevented that would be otherwise generated due to the above unstable laser oscillation. The light source 100 can output a light having an arbitrary wavelength between 1060 nanometers to 1200 nanometers by adjusting the transmission bands of the etalon filters 6a and 6b.

Because a semiconductor laser is used for the light source 100, the life of the light source 100 is several tens of thousands of hours and semipermanent use of the light source 100 is possible, i.e., the light source 100 can be economically excellent. In addition, because efficiency in energy conversion is high and no cooling device is required, the light source 100 can be downsized and economically excellent. Particularly, the light source 100 can be used in combination with an SHG element, which is configured to efficiently generate a harmonic light and has a narrow pumping wavelength band, as a light source for generating a light having a wavelength equal to or longer than 530 nanometers and equal to or shorter than 600 nanometers as a stable output that is required to a light source used for, for example, a laser microscope, a fluorescence analyzer for biomedicine, a biological analyzer for biomedicine, and a precision measurement device. Accordingly, a fluorescence analysis of various types of protein, which is conventionally considered difficult, can be performed.

Subsequently, a light source 100a according to a second embodiment of the present invention is explained. The light source 100a according to the second embodiment has a similar configuration to that of the light source 100 according to the first embodiment, and leads to similar effects to those of the first embodiment. However, the light source 100a according to the second embodiment is different from that of the first embodiment in that, for example, a distributed refractive index lens serves as a lens unit.

Figure 2:
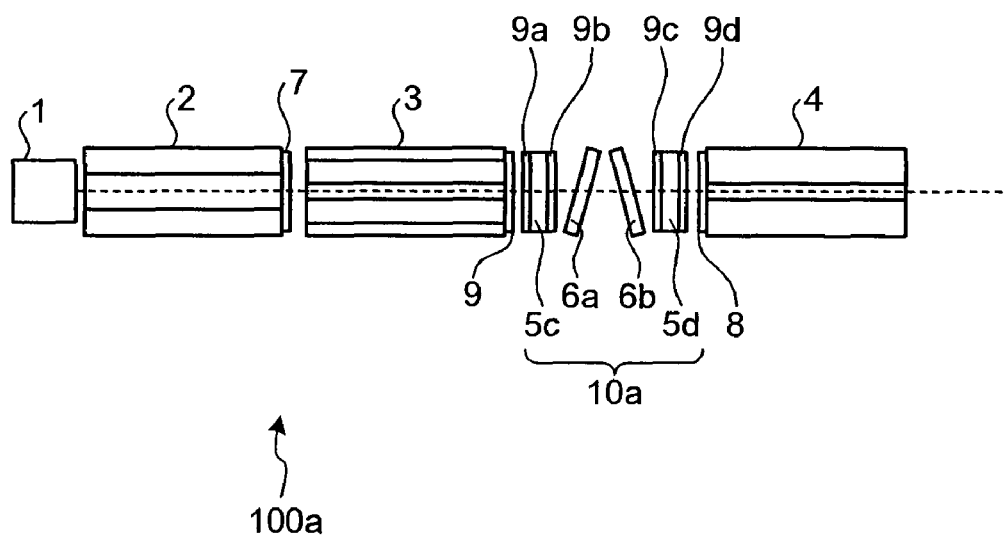
FIG. 2 is a schematic diagram of a light source according to a second embodiment of the present invention.

FIG. 2 is a schematic diagram of the light source 100a. A spatial coupling unit 10a of the light source 100a includes a distributed refractive index lenses 5c and 5d as a lens unit. Dielectric multilayer AR coatings 9a to 9d are formed on facets, from each of which a light is input or output, of the distributed refractive index lenses 5c and 5d, thereby preventing formation of an unnecessary resonator.

Because the spatial coupling unit 100a of the light source 100a according to the second embodiment includes the distributed refractive index lenses 5c and 5d as a lens unit, the spatial coupling unit can be downsized and the position of the optical system can be easily adjusted. Therefore, the light source 100a can be downsized and have high productivity.

Subsequently, a light source 100b according to a third embodiment of the present invention is explained. The light source 100b according to the third embodiment has a similar configuration to that of the light source 100 according to the first embodiment, and leads to similar effects to those of the first embodiment. However, the light source 100b according to the third embodiment is different from that of the first embodiment in that, for example, a spatial coupling unit includes a polarizer and a polarization-maintaining optical fiber serves as an output-light waveguide.

Figure 3:
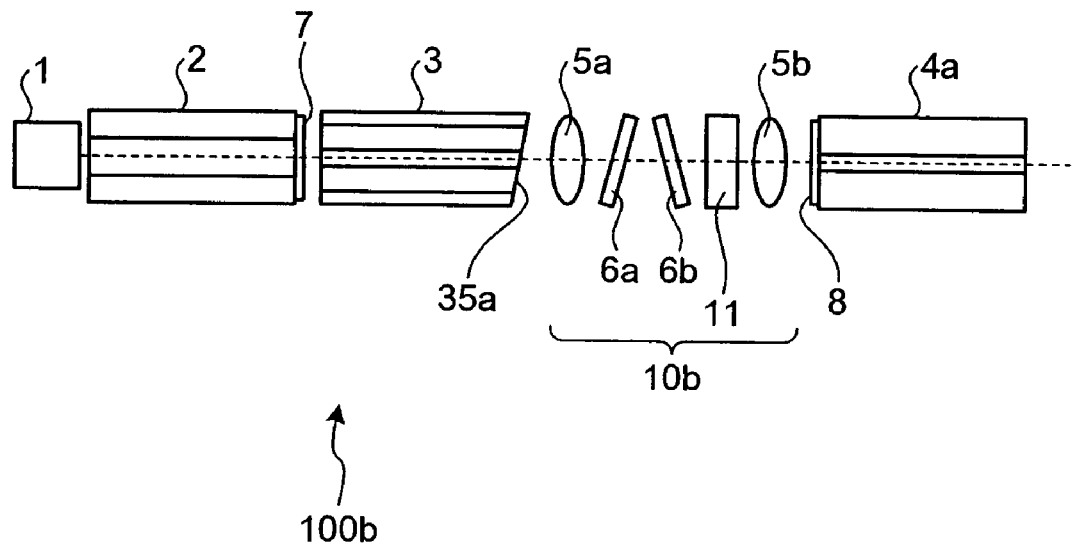
FIG. 3 is a schematic diagram of a light source according to a third embodiment of the present invention.

FIG. 3 is a schematic diagram of the light source 100b. A spatial coupling unit 10b of the light source 100b includes a polarization filter 11, and a polarization-maintaining optical fiber 4a serves as an output-light waveguide. The polarization filter 11 transmits a light having a specific linearly-polarized wave of a spontaneously-transmitted light input into the spatial coupling unit 10b. Accordingly, oscillation occurs only in a light in a specific linearly-polarized state. Meanwhile, the polarization maintaining optical fiber 4a is a so-called PANDA optical fiber that includes a core region having a core diameter equal to or larger than 5micrometers and equal to or smaller than 100 micrometers, a cladding region formed on an outer circumference of the core region and having an outer diameter equal to or smaller than 200 micrometers, which is larger than the core diameter, and a stress-applying member that is formed to be parallel to the core region such that the core region is interposed in the cladding region. The polarization maintaining optical fiber 4a guides the light input to the input facet while the polarization state of the light is maintained, and the light is output from the output facet. In addition, the output facet 35a of the double-clad optical fiber 3 is processed by abrasion to have an angle of 5 degrees to a plane perpendicular to that of the optical axis, thus preventing unnecessary reflection other than the reflection by the resonator. A long as the angle to the plane is equal to or more than four degrees, an effect of preventing occurrence of unnecessary reflection can be obtained.

Because of the above configuration, a laser light having a high extinction ratio, specifically, a laser light in the linearly-polarized state, can be output from the polarization-maintaining optical fiber 4a of the light source 100b. Therefore, even if generation efficiency of harmonic light generated by a harmonic generating element depends on the polarized state of the light source, the light source 100b can generate a harmonic light highly efficiently and stably.

Subsequently, a light source 100c according to a fourth embodiment of the present invention is explained. The light source 100c according to the fourth embodiment has a similar configuration to that of the light source 100b according to the third embodiment, and leads to similar effects to those of the third embodiment. However, the light source 100c according to the fourth embodiment is different from that of the third embodiment in that, for example, one filter realizes a wavelength selecting element and a polarizer.

Figure 4:
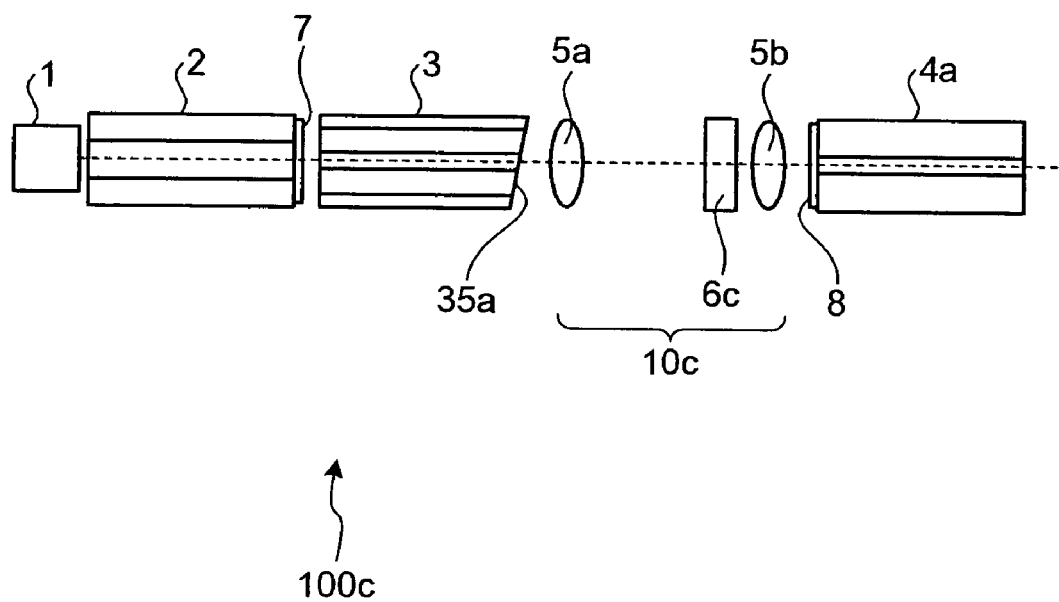
FIG. 4 is a schematic diagram of a light source according to a fourth embodiment of the present invention.

FIG. 4 is a schematic diagram of the light source 100c. A spatial coupling unit 10c of the light source 100c includes a polarization filter 6c that functions as an etalon filter. Specifically, the polarization filter 6c is a parallel plate having a thickness between approximately 20 micrometers to 30 micrometers. The surface of the polarization filter 6c is coated with a dielectric multilayer so that the spatial coupling unit 10c functions as an etalon filter. Because the polarization filter 6c is used in the light source 100c, the etalon filters 6a and 6b can be omitted. Accordingly, the light source 100 can be downsized and include a downsized spatial coupling unit.

Subsequently, a light source 200 according to a fifth embodiment of the present invention is explained. The light source 200 according to the fifth embodiment has a similar configuration to that of the light source 100b according to the third embodiment, and leads to similar effects to those of the third embodiment. However, the light source 200 according to the fifth embodiment is different from that of the third embodiment in that, for example, a fiber Bragg grating formed in an output-light waveguide serves as an output-side light reflecting unit.

Figure 5:
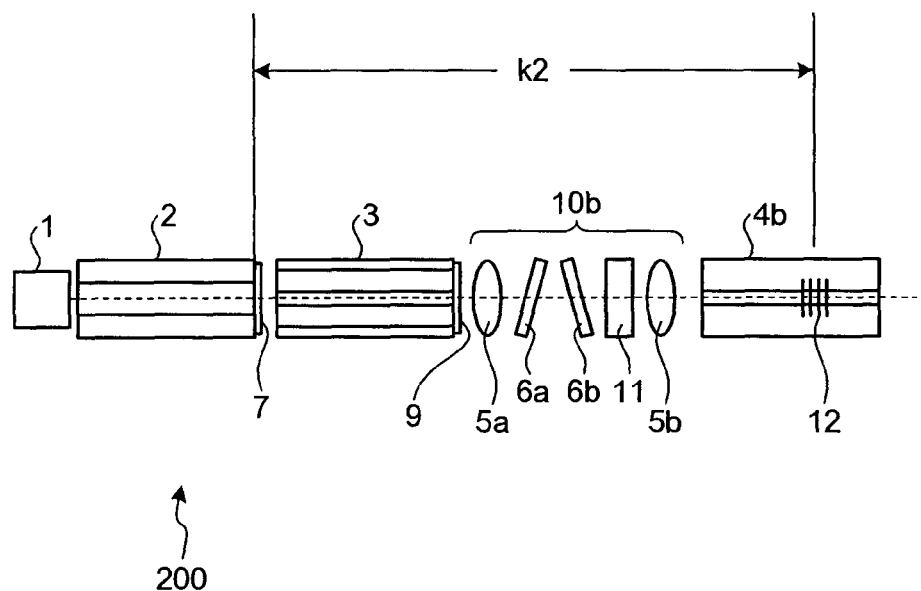
FIG. 5 is a schematic diagram of a light source according to a fifth embodiment of the present invention.

FIG. 5 is a schematic diagram of the light source 200. The spatial coupling unit 10b of the light source 200 includes the polarization filter 11, and a polarization-maintaining optical fiber 4b serves as an output light path. The polarization-maintaining optical fiber 4b includes a core region, a cladding region, and a stress applying member as the polarization-maintaining optical fiber 4a does. In addition, a fiber Bragg grating 12 is formed in the core region. The fiber Bragg grating 12 has a structure in which grating surfaces each perpendicular to the longitudinal direction of the core region are arranged at a predetermined pitch, and reflects a light having a full width half maximum of 10 nanometers and a wavelength of 1100 nanometers that is a transmission wavelength with respect to the etalon filters 6a and 6b by the Bragg reflection with a reflectivity equal to or more than 4% and equal to or less than 70%. The fiber Bragg grating 12 can be formed by phase masking in a way that a desired area along the longitudinal direction of the core region is irradiated with ultraviolet laser light. The reflectivity of the fiber Bragg grating 12 should preferably be equal to or more than 40% and equal to or less than 70% when the wavelength of the etalon filter is equal to or longer than 1075 nanometers, as in the case of the dielectric multilayer filter 8 according to the first embodiment.

The fiber Bragg grating 12 and the dielectric multilayer filter 7 of the light source 200 form a laser resonator k2. The fiber Bragg grating 12 reflects a light having a full width half maximum of 10 nanometers, thereby functioning also as a wavelength selecting element. Therefore, the light source 200 can output a linearly-polarized laser light. In addition, because of a synergistic effect of the fiber Bragg grating 12 and the etalon filters 6a and 6b, the light source 200 can and output a sharp laser light having a narrower full width half maximum. A fiber Bragg grating may cause an unnecessary reflection peak at a wavelength of a desired wavelength band due to a production condition. However, there is no risk that unstable laser oscillation is caused in the light source 200 because, even if such an unnecessary light is reflected, the etalon filters 6a and 6b block the unnecessary light.

Subsequently, a light source 200a according to a sixth embodiment of the present invention is explained. The light source 200a according to the sixth embodiment has a similar configuration to that of the light source 200 according to the fifth embodiment, and leads to similar effects to those of the third embodiment. However, the light source 200a according to the sixth embodiment is different from that of the fifth embodiment in that, for example, a distributed refractive index lens serves as a lens unit as in the case of the light source 100a according to the second embodiment.

Figure 6:
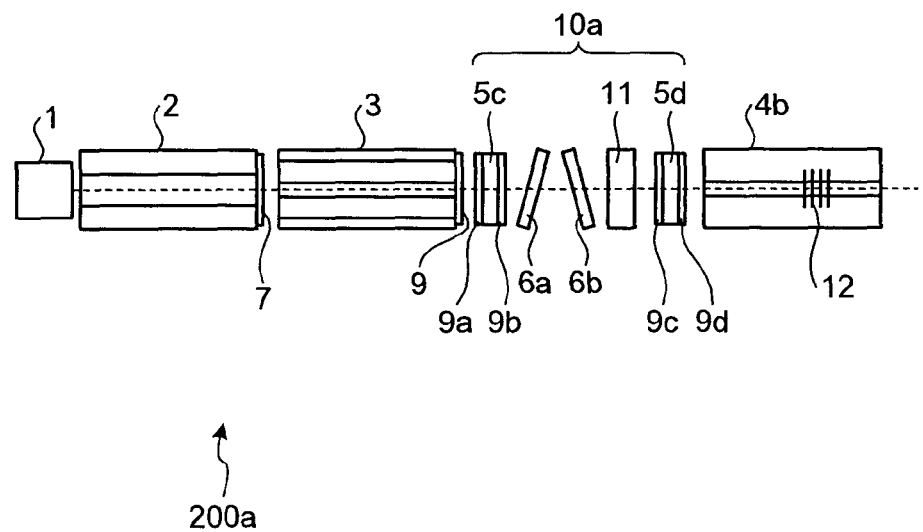
FIG. 6 is a schematic diagram of a light source according to a sixth embodiment of the present invention.

FIG. 6 is a schematic diagram of the light source 200a. As shown in FIG. 5, the fiber Bragg grating 12 of the light source 200a, which is formed in the polarization-maintaining optical fiber 4b, serves as an output-side light reflecting unit as in the case of the light source 200, and the spatial coupling unit 10a of the light source 200a includes the distributed refractive index lenses 5c and 5d as a lens unit as in the case of the light source 100a. The dielectric multilayer AR coatings 9a to 9d are formed on the facets, from each of which a light is input or output, of the distributed refractive index lenses 5c and 5d. Therefore, the light source 200a can output a linearly-polarized laser light and a sharp laser light having a narrower full width half maximum. In addition, the light source can be downsized and highly productive.

Subsequently, a light source 200b according to a seventh embodiment of the present invention is explained. The light source 200b according to the seventh embodiment has a similar configuration to that of the light source 200a according to the sixth embodiment, and leads to similar effects to those of the sixth embodiment. However, the light source 200b according to the seventh is different from that of the sixth embodiment in that, for example, a Bragg grating formed in an amplified-light waveguide serves as an input-side light reflecting unit.

Figure 7:
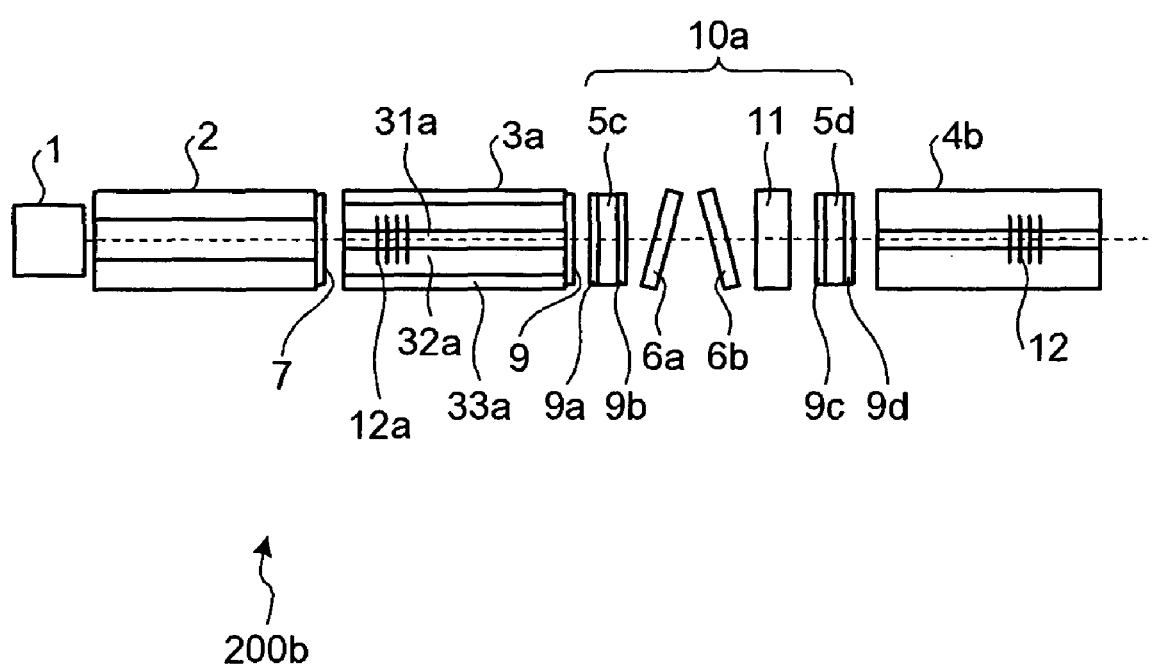
FIG. 7 is a schematic diagram of a light source according to a seventh embodiment of the present invention.

FIG. 7 is a schematic diagram of the light source 200b. As shown in FIG. 7, the fiber Bragg grating 12 of the light source 200b, which is formed in the polarization-maintaining optical fiber 4b, functions as an output-side light reflecting unit, and a fiber Bragg grating 12a of the light source 200b, which is formed in the double-clad optical fiber 3a, serves as an input-side light reflecting unit. The double-clad optical fiber 3a includes a core region 31a, an inner cladding layer 32a, and an outer cladding layer 33a that have characteristics similar to those of the double-clad optical fiber 3. The fiber Bragg grating 12a has characteristics similar to those of the fiber Bragg grating 12, and the fiber Bragg grating 12a can be formed as the fiber Bragg grating 12 is formed. The fiber Bragg grating 12a of the double-clad optical fiber 3a is formed on a side close to the multimode optical fiber 2.

The fiber Bragg grating 12 and the fiber Bragg grating 12a of the light source 200b form a laser resonator and also function as a wave selecting element. Therefore, the light source 200b can output a linearly-polarized laser light and a sharp laser light having a narrower full width half maximum.

Subsequently, a light source according to an eighth embodiment of the present invention is explained. The light source according to the eighth embodiment has a similar configuration to that of the light source according to the sixth embodiment, and leads to similar effects to those of the sixth embodiment. However, the light source according to the eighth embodiment is different from that of the sixth embodiment in that, for example, a pumping-light waveguide and an amplified-light waveguide are spliced with ferrules. The coupling portion is explained in detail below.

Figure 8:
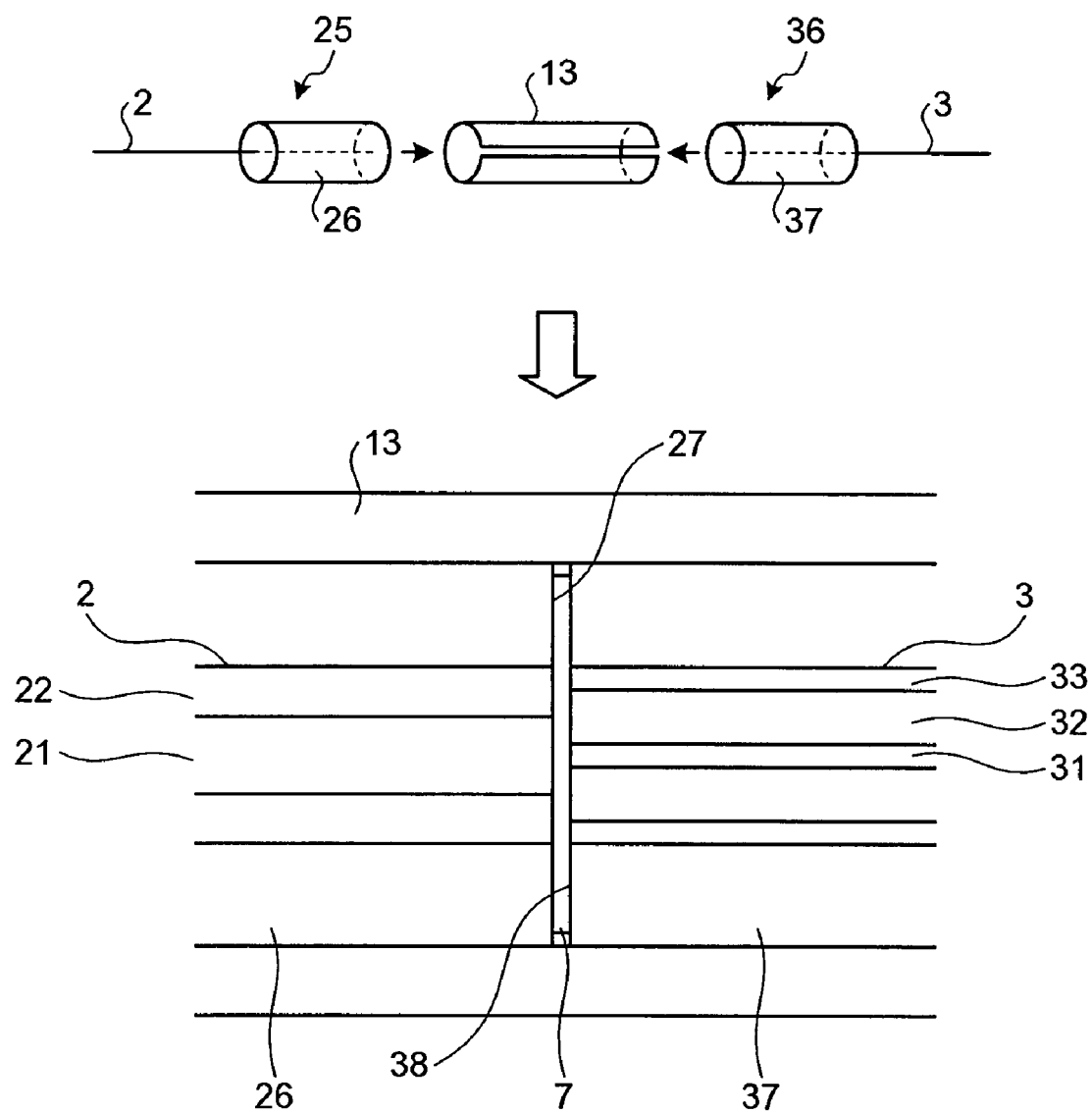
FIG. 8 is an external view of a coupling portion where a multimode optical fiber and a double-clad optical fiber of a light source according to an eighth embodiment of the present invention are spliced and an enlarged schematic diagram of the coupling portion.

FIG. 8 is an external view of the coupling portion where the multimode optical fiber 2 and the double-clad optical fiber 3 of the light source according to the eighth embodiment are spliced, and an enlarged schematic diagram of the coupling portion. As shown in the external view and the enlarged schematic diagram of FIG. 8, an end portion 25 on the output side of the multimode optical fiber 2 and an end portion 36 on the input side of the double-clad optical fiber 3 are stored in ferrules 26 and 37 that are cylindrical, and that are made of zirconia ceramics, in the light source according to the eight embodiment. The multimode optical fiber 2 or the double clad optical fiber 3 is inserted into any one of through holes formed on the central axis in the ferrules 26 and 37. The positions of the facets of the multimode optical fiber 2 and the double-clad optical fiber 3 are adjusted such that each of the ends of the multimode optical fiber 2 and the double-clad optical fiber 3 and a corresponding one of the ends of the ferrules 26 and 37 are on the same plane, and are fixed with an adhesive. Thereafter, the ends of the ferrules 26 and 37 are spliced by inserting the ferrules 26 and 37 from both ends of a split sleeve 13 into the split sleeve 13 that has a through hole having the same diameter as that of the outer diameters of the ferrules 26 and 37, and that is formed of zirconia ceramics. In this manner, the multimode optical fiber 2 and the double-clad optical fiber 3 are connected. Because the dielectric multilayer filter 7 is formed after the ferrule 26 is fixed to the multimode optical fiber 2 in the case of the eighth embodiment, the dielectric multilayer filter 7 is formed also on a facet 27 of the ferrule 26 as shown in the enlarged schematic diagram of FIG. 8. The reference numerals 27 and 38 respectively indicate facets of the ferrules 26 and 37.

Because the multimode optical fiber 2 and the double-clad optical fiber 3 of the light source according to the eighth embodiment of the present invention are connected in the above manner, the optical axes of the multimode optical fiber 2 and the double-clad optical fiber 3 easily match and can be inhibited from deviating. This reduces the connection loss. Furthermore, even if the attachment and detachment at the coupling portion are repeated, high reproducibility to compensate the coupling loss can be realized. An SC connector or an LC connector can be provided to each of the end portion on the output side of the multimode optical fiber 2 and the end portion on the output side of the double-clad optical fiber 3 to connect the multimode optical fiber 2 and the double-clad optical fiber 3 with the connectors via an SC adaptor or an LC adaptor that has a built-in sleeve.

Subsequently, a light source according to a ninth embodiment of the present invention is explained. The light source according to the ninth embodiment has a similar configuration to that of the light source according to the sixth embodiment, and leads to similar effects to those of the sixth embodiment. However, the light source according to a ninth embodiment is different from that of the sixth embodiment in that, for example, a light output facet of a multimode optical fiber has a convex surface and a dielectric multilayer filter serving as an input-side light reflecting unit is formed on the surface. The coupling portion is explained in detail below.

Figure 9:
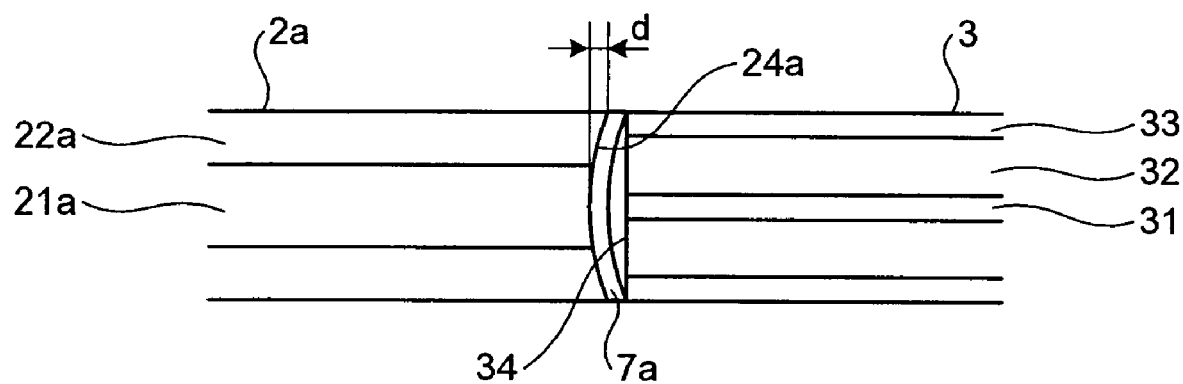
FIG. 9 is an enlarged schematic diagram of a coupling portion where a multimode optical fiber and a double-clad optical fiber of a light source according to an eighth embodiment of the present invention are spliced.

FIG. 9 is an enlarged schematic diagram of a coupling portion where a multimode optical fiber and a double-clad optical fiber of a light source according to the ninth embodiment are spliced. As shown in FIG. 9, an output facet 24a of the multimode optical fiber 2a of the light source according to the ninth embodiment, which includes the core region 21a and the cladding region 22a, has a concave surface having a depth d at a center portion, and the dielectric multilayer filter 7a serving as an input-side light reflecting unit is formed thereon. Therefore, the dielectric multilayer filter 7a can be prevented from being in contact with the input facet 34 of the double-clad optical fiber 3, and accordingly, the facet can be prevented from being damaged. Such a concave surface can be realized by polishing. If the depth d is equal to or more than 1 micrometer, the facets can be prevented from being in contact with, and it suffices that the depth d be equal to or smaller than 50 micrometers. At least one of the output facet of the multimode optical fiber and the input facet of the optical fiber of the double-clad optical fiber should preferably have a concave surface, because such a surface brings an effect of preventing damage on the facets.

The present invention is not limited to the present embodiments. According to the present embodiments, for example, Yb ions are employed as an amplification medium. However, ions of other rare-earth elements such as erbium (Er) or a combination of Yb ions and Er ions can be employed as an amplification medium. In the case where Er ions are used as an amplification medium, a semiconductor pumping laser is used that generates a pumping laser light having a wavelength of approximately between 980 nanometers and 1480 nanometers. In this case, the wavelength band of a spontaneous emission light is approximately between 1520 nanometers and 1610 nanometers. In the case where the combination of Yb ions and Er ions are used as an amplification medium, a semiconductor pumping laser is used that generates a pumping laser light having a wavelength of approximately between 900 nanometers and 1000 nanometers. In this case, the wavelength band of a spontaneous emission light is approximately between 1520 nanometers and 1610 nanometers as well.

According to the present embodiments, an etalon filter is used as a wavelength selecting element. Alternatively, a band path filter of a dielectric multilayer can be used that is formed by alternately depositing high-refractive dielectric films made of, for example, $Ta_2O_5$ and low-refractive dielectric films made of, for example, $SiO_2$ on a glass substrate. According to the present embodiments, the output facet of the double-clad optical fiber has an angle of 4 degrees to the plane perpendicular to the optical axis. It suffices that at least one of the facets of the pumping-light waveguide, the amplified-light waveguide, and the output-light waveguide, on which no dielectric multilayer filter serving as an input-side light reflecting unit or an output-side light reflecting unit is formed, has the above angle. In addition, it suffices that an antireflection coating is formed on any one of the facets of the pumping-light waveguide, the amplified-light waveguide, and the output-light waveguide, on which no dielectric multilayer filter serving as an input-side light reflecting unit or an output-side light reflecting unit is formed.

Furthermore, according to the present embodiments, a spherical lens or a distributed refractive index lens is used as a lens unit. Alternatively, a plano-convex lens, a graded index optical fiber, or an aspherical lens, or a combination thereof can be used.

In the case of the light source including the spatial coupling unit that includes the polarization filter according to the present embodiments, the polarization-maintaining optical fiber is used as the output-light waveguide. If a polarization-maintaining optical fiber is used as the amplified-light waveguide similarly, output of a light in a more stable polarization state can be obtained.

Moreover, according to the present embodiments, the dielectric multilayer filter serving as the input-side reflecting unit is formed on the output facet of the multimode optical fiber serving as the pumping-light output waveguide. Alternatively, the dielectric multilayer filter can be formed on the input facet of the double-clad optical fiber. Similarly, although the dielectric multilayer filter serving as the output-side light reflecting unit is formed on the input facet of the single-mode optical fiber serving as the output-light waveguide according to the present embodiments, the dielectric multilayer filter can be formed on the output facet. In addition, a dielectric multilayer that reflects a light having a wavelength of a pumping laser light with a reflectivity equal to or more than 4% and equal to or less than 20% can be formed on the output facet of the amplified-light waveguide. The dielectric multilayer can reflect back a part of the pumping laser light not having been used for excitation of the amplification medium to the amplified-light waveguide. This increases the efficiency of laser oscillation.

Furthermore, according to the present embodiments, the core diameter of the multimode optical fiber serving as the pumping-light waveguide should preferably be equal to or smaller than 400 micrometers. The reason is as follows. For example, a bundle fiber is formed that includes multimode optical fibers whose ends on one side are bundled, and that has a core diameter of 100 micrometers and a clad outer diameter of 125 micrometers, and the ends of the multimode optical fibers on the other side are attached to a plurality of semiconductor lasers. The double clad optical fiber is excited by the semiconductor lasers. In this case, that five or seven multimode optical fibers should preferably be bundled in consideration of light coupling efficiency. When the multimode optical fibers to be bundled are arranged most closely to each other, three of the multimode optical fibers are linearly arranged. If the core diameter of the multimode optical fiber serving as the pumping-light waveguide is 400 micrometers, the light output from the bundle fiber can be sufficiently joined. According to the present embodiments, the multimode optical fiber is used as the pumping-light waveguide. Alternatively, a single mode optical fiber can be alternatively used as the pumping-light waveguide.

As described above, according to an aspect of the present invention, by forming an amplified-light waveguide and a laser resonator, which includes a spatial coupling unit including a wavelength selecting element that selectively transmits a light having a desired wavelength band out of a spontaneous emission light generated in the amplified-light waveguide, a stable laser oscillation with a wavelength of a light that can be transmitted through the wavelength selecting element can be obtained so that an unnecessary light having the wavelength band of the spontaneous emission light is filtered to avoid an unstable laser oscillation. This brings an effect of realizing a light source that outputs a stable light.

Although the invention has been described with respect to a specific embodiment for a complete and clear disclosure, the appended claims are not to be thus limited but are to be construed as embodying all modifications and alternative constructions that may occur to one skilled in the art that fairly fall within the basic teaching herein set forth.

What is claimed is:

1. A light source comprising:
a semiconductor pumping laser that outputs a pumping laser light;
a pumping-light waveguide that guides the pumping laser light output from the semiconductor pumping laser;
an amplified-light waveguide that is connected to the pumping-light waveguide, and that is doped with an amplification medium that is pumped by the pumping laser light so that a spontaneous emission light in a desired wavelength band is generated;
an output-light waveguide that guides the spontaneous emission light output from the amplified-light waveguide;
a spatial coupling unit provided between the amplified-light waveguide and the output-light waveguide, the spatial coupling unit including
a wavelength selecting element that selectively transmits a light having a desired wavelength band out of the spontaneous emission light,
a lens unit that couples the spontaneous emission light to the wavelength selecting element, and
a polarizer that transmits a light of the spontaneous emission light with a predetermined polarization;
an input-side light reflecting unit that is provided between the semiconductor pumping laser and the amplified-light waveguide; and
an output-side light reflecting unit that is formed on an output side of the spatial coupling unit, wherein
the input-side light reflecting unit and the output-side light reflecting unit form a laser resonator that includes the amplified-light waveguide and the spatial coupling unit, and
the output-side light reflecting unit is a fiber Bragg grating formed on the output-light waveguide, and that selectively reflects a light in a wavelength band including a transmission wavelength of the wavelength selecting element.

2. A light source comprising:
a semiconductor pumping laser that outputs a pumping laser light;
a pumping-light waveguide that guides the pumping laser light output from the semiconductor pumping laser;
an amplified-light waveguide that is connected to the pumping-light waveguide, and that is doped with an amplification medium that is pumped by the pumping laser light so that a spontaneous emission light in a desired wavelength band is generated;
an output-light waveguide that guides the spontaneous emission light output from the amplified-light waveguide;
a spatial coupling unit provided between the amplified-light waveguide and the output-light waveguide, the spatial coupling unit including
a wavelength selecting element that selectively transmits a light having a desired wavelength band out of the spontaneous emission light,
a lens unit that couples the spontaneous emission light to the wavelength selecting element, and
a polarizer that transmits a light of the spontaneous emission light with a predetermined polarization;
an input-side light reflecting unit that is provided between the semiconductor pumping laser and the amplified-light waveguide; and
an output-side light reflecting unit that is formed on an output side of the spatial coupling unit, wherein
the input-side light reflecting unit and the output-side light reflecting unit form a laser resonator that includes the amplified-light waveguide and the spatial coupling unit, and
the output-side light reflecting unit is a filter formed on either one of an input facet and an output facet of the output-light waveguide.

3. A light source comprising:
a semiconductor pumping laser that outputs a pumping laser light;
a pumping-light waveguide that guides the pumping laser light output from the semiconductor pumping laser;
an amplified-light waveguide that is connected to the pumping-light waveguide, and that is doped with an amplification medium that is pumped by the pumping laser light so that a spontaneous emission light in a desired wavelength band is generated;
an output-light waveguide that guides the spontaneous emission light output from the amplified-light waveguide;
a spatial coupling unit provided between the amplified-light waveguide and the output-light waveguide, the spatial coupling unit including
a wavelength selecting element that selectively transmits a light having a desired wavelength band out of the spontaneous emission light,
a lens unit that couples the spontaneous emission light to the wavelength selecting element, and
a polarizer that transmits a light of the spontaneous emission light with a predetermined polarization;
an input-side light reflecting unit that is provided between the semiconductor pumping laser and the amplified-light waveguide; and
an output-side light reflecting unit that is formed on an output side of the spatial coupling unit, wherein the input-side light reflecting unit and the output-side light reflecting unit form a laser resonator that includes the amplified-light waveguide and the spatial coupling unit, and the input-side light reflecting unit is a filter formed on either one of an output facet of the pumping-light waveguide and an input facet of the amplified-light waveguide.

4. A light source comprising:

a semiconductor pumping laser that outputs a pumping laser light;

a pumping-light waveguide that guides the pumping laser light output from the semiconductor pumping laser;

an amplified-light waveguide that is connected to the pumping-light waveguide, and that is doped with an amplification medium that is pumped by the pumping laser light so that a spontaneous emission light in a desired wavelength band is generated;

an output-light waveguide that guides the spontaneous emission light output from the amplified-light waveguide;

a spatial coupling unit provided between the amplified-light waveguide and the output-light waveguide, the spatial coupling unit including
 a wavelength selecting element that selectively transmits a light having a desired wavelength band out of the spontaneous emission light,
 a lens unit that couples the spontaneous emission light to the wavelength selecting element, and
 a polarizer that transmits a light of the spontaneous emission light with a predetermined polarization;

an input-side light reflecting unit that is provided between the semiconductor pumping laser and the amplified-light waveguide; and an output-side light reflecting unit that is formed on an output side of the spatial coupling unit, wherein the input-side light reflecting unit and the output-side light reflecting unit form a laser resonator that includes the amplified-light waveguide and the spatial coupling unit, and the pumping-light waveguide is a multimode optical fiber having a core diameter equal to or larger than 50 micrometers and equal to or smaller than 400 micrometers.

5. A light source comprising:

a semiconductor pumping laser that outputs a pumping laser light;

a pumping-light waveguide that guides the pumping laser light output from the semiconductor pumping laser;

an amplified-light waveguide that is connected to the pumping-light waveguide, and that is doped with an amplification medium that is pumped by the pumping laser light so that a spontaneous emission light in a desired wavelength band is generated;

an output-light waveguide that guides the spontaneous emission light output from the amplified-light waveguide;

a spatial coupling unit provided between the amplified-light waveguide and the output-light waveguide, the spatial coupling unit including
 a wavelength selecting element that selectively transmits a light having a desired wavelength band out of the spontaneous emission light,
 a lens unit that couples the spontaneous emission light to the wavelength selecting element, and
 a polarizer that transmits a light of the spontaneous emission light with a predetermined polarization;

an input-side light reflecting unit that is provided between the semiconductor pumping laser and the amplified-light waveguide; and an output-side light reflecting unit that is formed on an output side of the spatial coupling unit, wherein the input-side light reflecting unit and the output-side light reflecting unit form a laser resonator that includes the amplified-light waveguide and the spatial coupling unit, and a reflection coating that reflects a light having the wavelength of the pumping laser light with a reflectivity equal to or higher than 4% and equal to or lower than 20% is formed on the output facet of the amplified-light waveguide.

6. A light source comprising:

a semiconductor pumping laser that outputs a pumping laser light;

a pumping-light waveguide that guides the pumping laser light output from the semiconductor pumping laser;

an amplified-light waveguide that is connected to the pumping-light waveguide, and that is doped with an amplification medium that is pumped by the pumping laser light so that a spontaneous emission light in a desired wavelength band is generated;

an output-light waveguide that guides the spontaneous emission light output from the amplified-light waveguide;

a spatial coupling unit provided between the amplified-light waveguide and the output-light waveguide, the spatial coupling unit including
 a wavelength selecting element that selectively transmits a light having a desired wavelength band out of the spontaneous emission light, and
 a lens unit that couples the spontaneous emission light to the wavelength selecting element;

an input-side light reflecting unit that is provided between the semiconductor pumping laser and the amplified-light waveguide; and an output-side light reflecting unit that is formed on an output side of the spatial coupling unit, wherein the input-side light reflecting unit and the output-side light reflecting unit form a laser resonator that includes the amplified-light waveguide and the spatial coupling unit, and at least one end portion of the pumping-light waveguide and at least one end portion of the amplified-light waveguide is respectively held in ferrules of a cylindrical shape such that ends of the ferrules and facets of the pumping-light waveguide and the amplified-light waveguide are on the same plane, and the pumping-light waveguide and the amplified-light waveguide are connected by inserting the ferrules into a sleeve having a through hole with a diameter same as an outer diameter of the ferrule from both ends of the sleeve and connecting the ends of the ferrules.

* * * * *